(12) United States Patent
Ramsey et al.

(10) Patent No.: US 6,238,858 B1
(45) Date of Patent: May 29, 2001

(54) TRANSGENOMIC VIRUSES

(75) Inventors: William J. Ramsey, Germantown; R. Michael Blaese; Kleanthis G. Xanthopoulos, both of Rockville, all of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/058,686

(22) Filed: Apr. 10, 1998

Related U.S. Application Data (60) Provisional application No. 60/043,667, filed on Apr. 11, 1997.

(51) Int. Cl.[7] .............................. C12Q 1/70; C12P 21/04; C12N 15/00; A61K 39/12
(52) U.S. Cl. ......................... 435/5; 435/70.1; 435/320.1; 424/199.1
(58) Field of Search ........................ 435/5, 70.1, 320.1; 424/199.1

(56) References Cited

U.S. PATENT DOCUMENTS 5,589,377  12/1996  Lebkowski et al. .............. 435/240.2

FOREIGN PATENT DOCUMENTS

| WO 95/23867 | 9/1995 | (WO) | ............................ C12N/15/86 |
| WO 97/25466 | 7/1997 | (WO) | ............................ C12Q/1/70 |
| WO 98/22143 | 5/1998 | (WO) . | |

OTHER PUBLICATIONS

Bunnell et al., "Retrovirus–Mediated Gene Transfer", In Viral Genome Methods (Adolph ed), pp. 3–21 (1996).

Li et al., "Production of infections recombinant Moloney murine leukemia virus particles in BHK cells using Semliki Forest virus–derived RNA expression vectors", Proc. Natl. Acad. Sci., 93:11658–11663 (1996).

Fisher et al., "A Novel Adenovirus–Adeno–Associated Virus Hybrid Vector That Displays Efficient Rescue and Delivery of the AAV Genome", Human Gene Therapy 7:2079–2087, (1996).

Feng et al., "Stable in vivo gene trasnduction via a novel adenoviral/retroviral chimeric vector", Nature Biotechnology 15:866–870 (1997).

Richard G. Vile, "A marriage of viral vectors", Nature Biotechnology, 15:840–841 (1997).

Kathleen L. Berkner, "Development of Adenovirus Vectors for the Expression of Heterologous Genes", BioTechniques 6:(7) 616–629 (1988).

Naldini et al., "In Vivo Gene Delivery and Stable Transduction of Nondividing Cells by a Lentiviral Vector", Science 272:263–267 (1996).

Liljestrom et al., "A New Generation of Animal Cell Expression Vectors Based on the Semliki Forest Virus Replicon", Biotechnology 9:1356–1361 (1991).

Fassati et al., "Retroviral Vectors", Molecular and Cell Biology of Human Gene Therapeutics, 1–19 (1995).

A. Dusty Miller, "Retrovirus Packaging Cells", Human Gene Therapy 1: 5–13 (1995).

(List continued on next page.)

Primary Examiner—Hankyel T. Park
(74) Attorney, Agent, or Firm—Townsend and Townsend and Crew LLP (57) ABSTRACT

The present invention provides chimeric primary viruses, which are capable of producing secondary viruses in a producer host cell, and methods of making the same.

39 Claims, 1 Drawing Sheet

OTHER PUBLICATIONS

Chroboczek et al., "The Sequence of the Genome of Adenovirus Type 5 and the Comparison with the Genome of Adenovirus Type 2", *Virology* 186 280–285 (1992).

Shinnick et al., "Nucleotide sequence of Moloney murine leukaemia virus", *Nature* 293: 543–548, (1981).

Ott et al., "Sequence Aalysis of Amphotropic and 10A1 Murine Leukemia Viruses: Close Relationshi Mink Cell focus–Inducing Viruses", *Journal of Virology,* 64:(2) 757–766, (1990).

Arai, et al., "A New System for Stringent, High–titer Vesicular Stomatitis Virus G Protein–Pseudotyped Retrovirus Vector Induction by Introduction of Cre Recombinase into Stable Prepackaging Cell Lines," *Journal of Virology* (1998) 72(2): 1115–1121.

Bilbao, et al., "Adenoviral/retroviral vector chimeras: a novel strategy to achieve high–efficiency stable transduction in vivo," *The FASEB Journal* (1997) 11: 624–634.

Feng et al., "Stable in vivo gene transduction via a novel adenoviral/retroviral chimeric vector," *Nature Biotechnology* (1997) 15: 866–870.

Lin, "Construction of new retroviral producer cells from adenoviral and retroviral vectors," *Gene Therapy* (1995) 5: 1251–1258.

TRANSGENOMIC VIRUSES

CROSS-REFERENCE TO RELATED APPLICATIONS

This application claims priority to U.S. patent application Ser. No. 60/043,667, filed Apr. 11, 1997, herein incorporated by reference.

FEDERALLY SPONSORED RESEARCH OR DEVELOPMENT

Not applicable.

FIELD OF THE INVENTION

The present invention relates to chimeric primary viruses that are capable of producing secondary virus in a producer cell, and a method of making the same.

BACKGROUND OF THE INVENTION

The development of eukaryotic viral vectors has generally focused on delivery of one or more heterologous genes to target cells, particularly for gene therapy applications. A wide variety of viruses have been studied as potential eukaryotic viral vectors, e.g., adenovirus, herpes simplex virus, vaccinia virus, adeno-associated virus, and retrovirus (see, e.g., Berkner, *Biotechniques* 6: 616–629 (1988); Fisher et al., *Human Gene Therapy* 7: 2079–2087 (1996); and Fassati et al., *Retroviral Vectors, Molecular and Cell Biology of Human Gene Therapeutics* pp. 1–19 (Dickson ed., 1995)). Each of the vector systems has focused on a strategy that involves: (1) construction of a replication deficient viral vector by removing essential viral genes; (2) replacing these viral genes with a heterologous gene; and (3) transfecting the viral vector into a packaging cell line that complements the deleted viral genes, producing replication deficient viral particles.

Of all the viral vector systems studied to date, retroviral based systems remain the most popular. Retroviral vectors are useful because the genes they transduce are integrated into the genome of target cells, providing long term, stable expression of the heterologous gene. However, retroviral based vector systems have a number of problems. Most importantly, viral titers of retroviral particles produced from packaging cells are low, on the order of $10^6$–$10^7$ viral particles/ml. In addition, the retrovirus particle often stimulates an immune response because it is derived from a "non-self" packaging cell line.

Other viral based systems have encountered related difficulties. For example, although packaged adenovirus generally has high titers, the viral genome is episomal and transient. In addition, the virus induces an immune response, particularly in the majority of the human population that has been previously infected with this common virus. Similarly, both HSV and vaccinia vectors often provoke an immune response, particularly in those humans that either have been previously exposed to the virus or who have been immunized against the virus.

Adeno-associated viruses (AAV) are naturally occurring replication deficient viruses of the Dependovirus genus, Parvoviridae family. AAV vectors have also been investigated as potential eukaryotic viral vectors. These viruses require co-infection with a helper virus, typically adenovirus or HSV, for production of AAV viral particles from an infected cell. The AAV genome contains two genes, rep, necessary for replication of the viral genome, and cap, a virion protein. These genes are expressed once the AAV particle has infected a target cell.

Recently, Fisher et al., supra, described a vector that is a hybrid between adenovirus and AAV. This hybrid was created by first constructing a replication deficient adenovirus vector that contained an AAV genome, in which the rep and cap genes were replaced by the β-galactosidase gene. Second, this hybrid vector was transfected into 293 host cells, which packaged the adenovirus-AAV hybrid vector into an adenovirus particle. Rep and cap were provided as a separate plasmid tethered to the outside of the adenovirus particle via a polylysine bridge. Finally, this hybrid adenovirus was then used to infect producer host cells. Transient expression of rep by the tethered plasmid allowed rescue and replication of the AAV genome, and production of AAV particles.

However, this system fails to solve the problem of low virus titers and transduction efficiency. The AAV genome lacks the rep and cap genes, expression of which are necessary for efficient AAV replication and integration in the target cell after infection by an AAV virus particle. Instead, a low proportion of the AAV particles contain the rep protein expressed from the tethered plasmid. Thus, few infectious AAV particles are produced from this hybrid system. In addition, rep expression is generally toxic to cells. International patent application PCT/FR95/00233 describes a similar system, with similar defects.

Eukaryotic viral vectors have many applications beyond gene therapy, although these applications have not been extensively investigated. For example, previous studies have suggested that defective retroviral genomes (e.g., defective for gag, pol, or env genes, or the splice signals of the replication competent retroviruses) can be "rescued" from the genomic DNA of cells by infection with replication competent retroviruses, which transcomplement and package the defective retroviral genomes (Wilkinson et al., *Endogenous Human Retroviruses*, in *The Retroviridae* (Levy, ed., 1994)). This rescue could provide an important means of diagnosing new disease caused by unknown viruses. However, this rescue is complicated by the difficulty of identifying the defective genomes in the midst of the large number of wild type replication competent retrovirus genomes.

Accordingly, there is a need for improved eukaryotic viral vectors for diagnostic applications and for delivering heterologous genes to cells in vitro, ex vivo, and in vivo. This invention fulfills these and other needs.

SUMMARY OF THE INVENTION

The present invention therefore provides novel chimeric primary viruses, which infect producer host cells and direct the production of secondary viruses. The chimeric primary viruses have a high transduction efficiency and readily infect the producer cells. The secondary viruses produced in this manner have a high viral titer and therefore are able to efficiently infect target host cells. In addition, the secondary viruses can be made in producer cells that are from the same source as the target cells, thus producing secondary viruses that are autologous and therefore evade the immune response.

The use of system of the present invention would also overcome the problem of unknown viral genome rescue. Chimeric primary viruses are constructed that encode all the packaging components necessary to rescue and package a viral genome. The chimeric primary virus is used to infect a cell line that may contain an unknown viral genome. This genome need only contain the necessary packaging signal for recognition by the packaging components produced by the chimeric primary virus. The packaging components transcomplement the viral genome to produce a replication deficient secondary virus. Such packaged viral particles contain only the rescued viral genome, since the chimeric primary virus does not include a secondary viral genome, but only the necessary packaging genes. The secondary virus containing the unknown genome is then collected from the cell supernatant and either analyzed directly or used to infect target cells. The target cells may be packaging cells that allow for further production of the secondary virus containing the unknown viral genome.

In one aspect, the present invention provides a system for producing secondary viruses in producer host cells for subsequent infection of target cells. This system comprises chimeric primary viruses or a combination of such viruses that are either individually or collectively genetically competent to direct the production of secondary viruses in the producer host cells. These secondary viruses are capable of subsequently infecting target host cells, followed either by production of a lytic infection or integration of the viral genome. These secondary viruses are any virus other than the primary virus and are any virus other than a Dependovirus or a recombinant derivative of a Dependovirus.

In one embodiment, the producer host cells are autologous producer host cells and the target cells are autologous target cells. In another embodiment, the target cell is selected from the group consisting of embryonic cell and sperm cell. In another embodiment, the secondary virus is isolated from the producer host cell.

In one embodiment, the secondary virus is replication deficient. In another embodiment, the secondary virus comprises a nucleic acid capable of being integrated into the genome of the target cell.

In one embodiment, the secondary virus comprises an expression cassette comprising a nucleic acid encoding a heterologous protein or antisense nucleic acid. In another embodiment, the heterologous protein is selected from the group consisting of hormones, cell receptors, and enzymes. In another embodiment, the heterologous protein is selected from the group consisting of Factor IX and CFTR.

In one embodiment, the primary virus is an adenovirus. In another embodiment, the secondary virus is a togavirus, preferably an alphavirus. In yet another embodiment, the secondary virus is selected from the group consisting of Semliki Forest virus and Sindbis virus. In another embodiment, the secondary virus is a retrovirus, preferably an oncornavirus or a lentivirus.

In another aspect, the invention provides a method for producing secondary viruses in producer host cells for subsequent infection of target cells, comprising the steps of: (1) contacting the producer host cells with chimeric primary viruses, which individually or collectively are able to direct the production of secondary viruses in the producer host cells; and (2) incubating the producer host cells for a time sufficient for the chimeric primary viruses to infect the producer host cells and to direct the production of the secondary viruses for infection of target cells. The secondary viruses produced by this method are any virus other than the primary viruses and any virus other than an Dependovirus or a recombinant derivative thereof.

In one embodiment, the method further includes the step of infecting target cells with the secondary viruses, followed by either integration of the viral genome of by production of a lytic infection. In another embodiment, the method further comprises the step of isolating the secondary viruses.

Other embodiments of this method include those described above for the system of the invention.

In another aspect, the invention provides a method of isolating an unknown viral genome from a host cell, comprising the steps of: (1) contacting the host cell with chimeric primary viruses, which individually or collectively are able to produce replication deficient secondary viruses; (2) incubating the host cell for a time sufficient for the chimeric primary viruses to infect the host cell and to produce packaging components; and (3) rescuing the unknown viral genome by packaging the it to produce replication deficient secondary virus. This secondary virus is any virus other than the primary virus and any virus other than a Dependovirus or a recombinant derivative thereof.

In one embodiment, the method further comprises the step of isolating the unknown viral genome. In another embodiment, the method further comprises the step of infecting a target cell with the replication deficient secondary virus.

In one embodiment, the primary virus is an adenovirus. In another embodiment, the unknown viral genome is a retrovirus, preferably an oncornavirus or a lentivirus.

In another aspect, the present invention provides a system for producing secondary viruses in complementary producer host cells for subsequent infection of target cells. This system comprises chimeric primary viruses or a combination of such viruses that in combination with the complementary producer host cells are either individually or collectively genetically competent to direct the production of secondary viruses in the complementary producer cells. These secondary viruses are capable of subsequently infecting target host cells, followed either by production of a lytic infection or integration of the viral genome. These secondary viruses are any virus other than the primary virus and are any virus other than a Dependovirus or a recombinant derivative of a Dependovirus.

In another aspect, the invention provides a method for producing secondary viruses in complementary producer host cells for subsequent infection of target cells, comprising the steps of: (1) contacting the complementary producer host cells with chimeric primary viruses, which in combination with the complementary producer host cells are individually or collectively able to direct the production of secondary viruses in the complementary producer host cells; and (2) incubating the complementary producer host cells for a time sufficient for the chimeric primary viruses to infect the complementary producer host cells and to direct the production of the secondary viruses for infection of target cells. The secondary viruses produced by this method are any virus other than the primary viruses and any virus other than an Dependovirus or a recombinant derivative thereof.

DETAILED DESCRIPTION

A. Introduction

Figure 1:
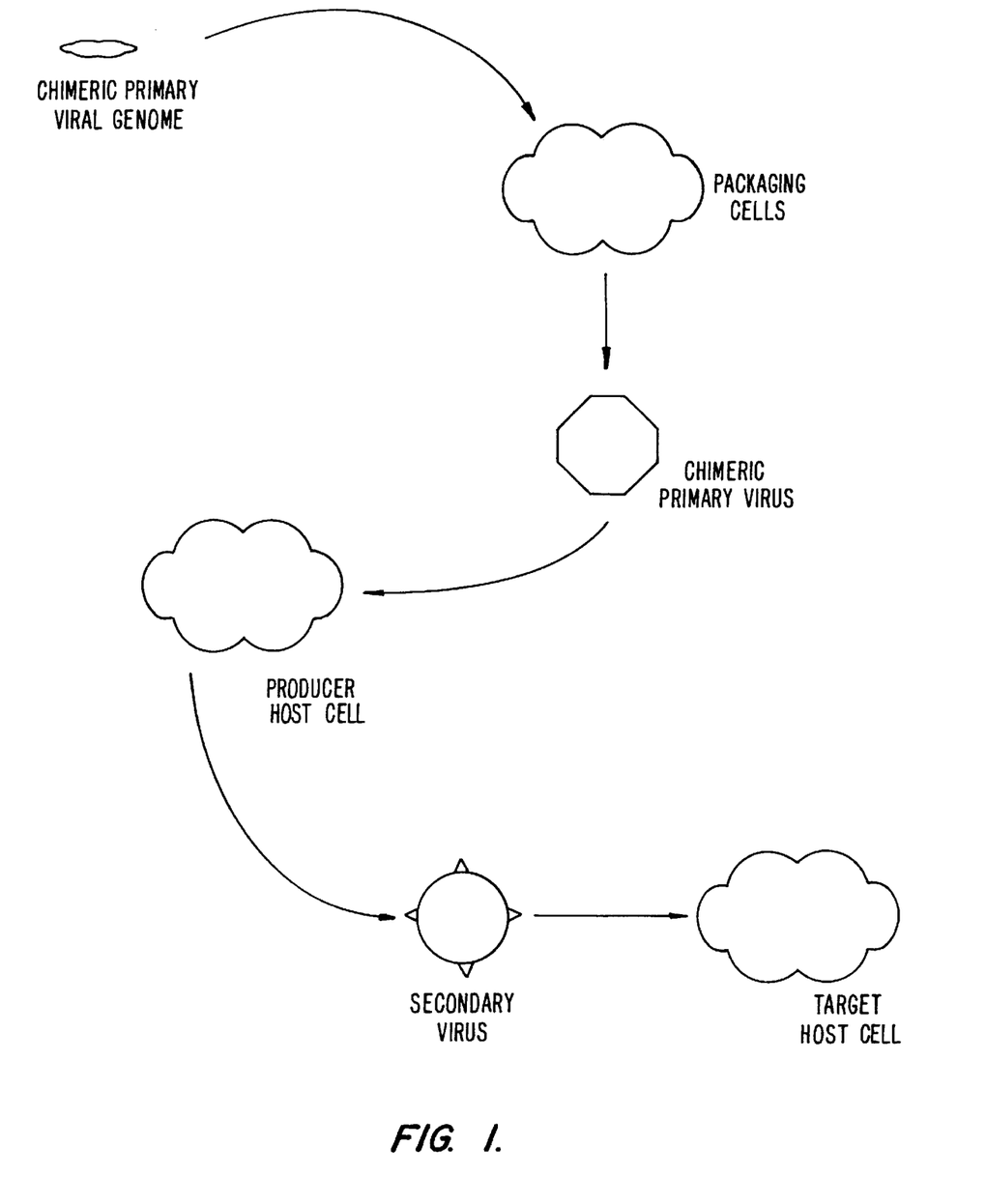
FIG. 1: This figure depicts the steps of packaging a chimeric primary viral genome, infecting producer host cells with primary chimeric virus, producing secondary virus, and subsequently infecting target host cells with secondary virus.

The development of eukaryotic viral vectors has been hampered by low titers of viral stocks and host range restrictions caused by the host immune system. The present invention provides systems and methods for producing chimeric primary viruses that overcome these difficulties. In this system, a "chimeric" primary viral genome is constructed that contains nucleic acid sequences from two different viruses, a primary virus and a secondary virus. This chimeric viral genome is packaged into a chimeric primary virus and then used to transduce a producer host cell. Then chimeric primary virus then produces secondary virus. The host cells that are infected by the chimeric primary virus thus become efficient producer cells for the secondary virus. These secondary viruses are capable of subsequently infecting target host cells. Because the producer cell and the target cell can come from the same source, the secondary virus can evade the host immune system. Such secondary viruses can also contain a heterologous gene for expression in the target cell.

In a variation on this system, the chimeric primary viruses infect producer cells that provide secondary packaging components in trans. Thus, in this system, the chimeric primary virus does not independently direct the production of the secondary virus. Instead, the producer cells complement the chimeric primary virus in trans to produce secondary virus. Suitable producer cells for this system include known packaging cell lines such as the retroviral packaging cell lines FLYA13 and ψ2. These cells contain genes encoding retroviral packaging components such as gag, pol, and env that complement the genes encoded by the chimeric primary virus.

These systems are useful for diagnostic applications such as rescuing unknown viral genomes from mammalian cells and determining their relationship to mammalian disease conditions. In addition, these systems are useful for efficiently developing transgenic non-human animals that express a heterologous gene, and for in vivo and ex vivo gene therapy.

B. Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, preferred methods and materials are described. As used herein, the following terms have the meanings ascribed to them unless specified otherwise.

A "chimeric primary virus" is a virus that includes nucleic acid sequences from two different viruses, a primary virus and a secondary virus. The term "chimeric primary virus" is used to refer to the packaged chimeric primary virus particle, while the term "chimeric primary viral genome" refers to the nucleic acid sequence that is packaged into the chimeric primary virus. The chimeric primary virus is capable of transducing a producer host cell and directing production of a secondary virus. The components of the chimeric primary viral genome include, but are not limited to, the following: (1) primary virus nucleic acid sequences that allow packaging into a primary virus particle, e.g., packaging signals; (2) optionally, secondary virus genes that encode proteins for packaging the genome of a secondary virus; (3) optionally, a secondary virus genome; (4) optionally, an expression cassette with a heterologous gene operably linked to a promoter, typically part of the secondary virus genome. The chimeric primary viral genome is typically packaged into a chimeric primary virus using packaging cells that complement the primary virus nucleic acid sequences. The chimeric primary virus can be replication deficient.

Chimeric primary viruses can provide the components of the secondary virus either in trans through a combination of chimeric primary viruses or from an individual chimeric primary virus, e.g., either "individually or collectively." In this manner, the primary chimeric viruses are "genetically competent to direct production of a secondary virus." The phrase "genetically competent to direct production of secondary viruses" includes rescue of an unknown viral genome with secondary virus packaging components provided by the chimeric primary virus. When a unknown viral genome is rescued, a "replication deficient secondary virus" is produced.

Alternatively, the chimeric primary viruses can provide the components of the secondary virus in combination with "complementary producer host cells". In this manner, the chimeric primary virus and the complementary producer cell in combination are "genetically competent to direct production of secondary viruses." Such complementary producer cells provide some or all of the packaging components necessary for packaging a viral genome and complement secondary virus components produced by the chimeric primary virus.

A "secondary virus" is a virus that is produced from a chimeric primary virus and is capable of subsequently transducing a target host cell. The term "secondary virus" is used to refer to the packaged secondary virus particle. The polynucleotide sequences of the secondary virus are derived from a virus that is different from the primary virus and are any virus other than a Dependovirus. The components of the secondary virus include, but are not limited to, the following: (1) secondary virus packaging components; (2) a secondary viral genome, which can be provided by the chimeric primary virus or rescued from the producer cell; (3) optionally, an expression cassette with a heterologous gene operably linked to a promoter, which is part of the secondary viral genome.

A "producer cell" or a "producer host cell" or a "complementary producer host cell" is a cell that has been transduced by a chimeric primary virus. The chimeric primary virus directs production of secondary virus in the producer host cell. A "complementary producer host cell" provides secondary virus packaging components in trans with the chimeric primary virus.

A "target cell" or a "target host cell" is a cell that is capable of being infected by a secondary virus. The secondary virus either produces a lytic infection in the target host cell or integrates its genome into the DNA of the target host cell.

An "embryonic cell" refers to a non-human mammalian embryonic cell.

The term "transduction" refers to the ability of a virus to enter a cell via infection, internalization, transfection or any other means.

A cell is "contacted" with a virus when the virus is associated with the cell so that the virus is capable of transducing the cell.

The term "integration" and "capable of being integrated" refer to the ability of secondary viruses to integrate their genome into the DNA of a target cell.

The term "production of a lytic infection" refers to the ability of a secondary virus to infect and transiently express gene products without integration of the viral genome into the host cell chromosome. Often the transient expression is at high levels, and can be used to produce high levels of heterologous gene expression. The lytic infection optionally results in lysis of the cell.

An "unknown virus" and an "unknown viral genome" refer to a viral genome that is present a producer host cell, which minimally includes any necessary packaging sequence so that it can be "rescued," e.g., packaged into a secondary virus. A packaging signal is any nucleic acid sequence that is required for specific packaging of the viral genome into a viral particle, e.g., "ψ" refers to a retroviral packaging signal that directs efficient and specific encapsidation of RNA into retroviral particles. Virus genome refers to DNA and RNA viral genomes, and to genomes that are episomal or integrated into the host cell DNA. Often, an RNA viral genome that contains a packaging sequence is transcribed from a DNA proviral genome that is integrated into the host cell DNA. The promoter may be a viral promoter, e.g, an LTR, or a cellular promoter.

An "autologous" cell refers to the relationship between cells derived from the same individual. Thus, a virus that is coated with a cell membrane is also considered autologous with respect to the producer cell that produced it and with respect to other cells from the same individual, e.g., target cells.

The retroviral gene "pol" encodes reverse transcriptase (RT). RT has several activities, including reverse transcription and RNase H activity, that are necessary for transcribing the retroviral RNA genome into provirus DNA. Pol also encodes "integrase," a protein involved in provirus integration into the host genome. RT and integrase proteins are packaged into the infective virion particle along with the retroviral RNA genome. The retroviral gene "gag" encodes "gag proteins" that are viral capsid proteins. The retroviral gene env encodes "envelope proteins," which are viral envelope proteins.

The term "packaging components" or "secondary virus packaging components" refers to any proteins or nucleic acid molecules required for assembling a viral genome into an infectious viral particle. For example, the packaging components required to assemble a retroviral RNA genome into an infectious retroviral particle include the proteins encoded by gag, pol, and env. A virus is "able to package a genome" when it produces the components necessary for packaging a genome, e.g., gag, pol, and env. The viral genome that is packaged by a virus that is "able to package a viral genome" may be provided either by the virus that is able to package to viral genome or the host cell. Alternatively, the some or all of the packaging components can be provided by complementary packaging cells.

"Replication deficient" refers to a chimeric primary virus that is not capable on its own of producing primary virus for subsequent infection cycles. The term also refers to secondary virus that is not capable on its own of producing subsequent secondary virus. Thus, a replication deficient virus can infect a cell but is not independently capable of producing further infectious viral particles of the same type. A replication deficient virus can lack any component necessary to replicate and produce an infectious viral particle. For example, it may lack genes that provide enzymatic functions or structural proteins, e.g., the retroviral gag, pol, and env genes, or the adenoviral E1A gene.

"Packaging cells" help replication-deficient viruses or viral genomes, which lack viral genes that have been replaced, e.g., by an expression cassette, to form virus particles that are capable of infecting another host cell. Such cells include 293 cells, which package adenovirus, and ψ2 cells or PA317 cells, which package retrovirus. Typically, a nucleic acid encoding a viral genome is introduced into a cell and is then packaged into a viral particle. Some packaging cells contain mutations so that they cannot supply virus genomes to produce infective particles; these packaging cells typically complement a viral genome to produce infective virus particles. Some packaging cells may also provide a viral genome that is packaged to produce infectious viral particles.

"Polynucleotide" and "nucleic acid" refer to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

A "heterologous polynucleotide sequence" or a "heterologous nucleic acid" is a relative term referring to a polynucleotide that is functionally related to another polynucleotide, such as a promoter sequence, in a manner so that the two polynucleotide sequences are not arranged in the same relationship to each other as in nature. Heterologous polynucleotide sequences include, e.g., a promoter operably linked to a heterologous nucleic acid, including a gene or a transcription unit, e.g., a nucleic acid encoding an antisense nucleic acid. Heterologous polynucleotide sequences are considered "exogenous" because they are introduced to the host cell via transformation, transduction, or infection techniques. However, the heterologous polynucleotide can originate from a foreign source or from the same source. Modification of the heterologous polynucleotide sequence may occur, e.g., by treating the polynucleotide with a restriction enzyme to generate a polynucleotide sequence that can be operably linked to a regulatory element. Modification can also occur by techniques such as site-directed mutagenesis.

"Recombinant" refers to polynucleotides constructed, synthesized or otherwise manipulated in vitro ("recombinant nucleic acids") and to methods of using recombinant nucleic acids to produce gene products encoded by those nucleic acids in cells, viruses, or other biological systems. For example, a cloned nucleic acid may be inserted into a suitable expression vector, and the vector can be used to produce a recombinant immunoglobulin fragment. A host cell that comprises the recombinant nucleic acid is referred to as a "recombinant host cell." The nucleic acid is then expressed in the recombinant host cell to produce, e.g., a "recombinant protein." A recombinant nucleic acid may serve a non-coding function (e.g., promoter, origin of replication, ribosome-binding site, etc.) as well.

An "expression cassette" refers to a series of nucleic acid elements that permit transcription of a gene or polynucleotide in a host cell. Typically, the expression cassette includes a promoter and a heterologous nucleic acid sequence that is transcribed. Expression cassettes may also include, e.g., transcription termination signals, polyadenylation signals, and enhancer elements. An expression cassette can be an "autocatalytic" expression cassette. In this case, the expression cassette includes the NSP1–4 alphavirus genes operably linked to a promoter, and the alphavirus subgenomic promoter operably linked to a gene. The NSP1–4 proteins encode replicase, which recognizes and transcribes the subgenomic promoter at high levels.

Expression cassettes are often included in an "expression vector," "cloning vector," or "vector," terms which usually refer to viruses, plasmids or other nucleic acid molecules that are able to transduce and/or replicate in a chosen host cell.

A "promoter" is an array of nucleic acid control sequences that direct transcription of an associated nucleic acid, which may be heterologous. A promoter includes nucleic acid sequences near the start site of transcription, such as a polymerase binding site. The promoter also optionally includes distal enhancer or repressor elements which can be located as much as several thousand base pairs from the start site of transcription.

The term "operably linked" refers to a functional relationship between two parts in which the activity of one part (e.g., the ability to regulate transcription) results in an action on the other part (e.g., transcription of the sequence). Thus, a nucleic acid is "operably linked to a promoter" when there is a functional linkage between a nucleic acid expression control sequence (such as a promoter or other transcription regulation sequences) and a second nucleic acid sequence (e.g., a native or a heterologous polynucleotide), where the expression control sequence directs transcription of the nucleic acid.

An "antisense" nucleic acid refers to a polynucleotide that is complementary to a target sequence of choice and capable of specifically hybridizing with the target molecules. The term antisense includes a "ribozyme," which is a catalytic RNA molecule that cleaves a target RNA through ribonuclease activity. Antisense nucleic acids hybridize to a target polynucleotide and interfere with the transcription, processing, translation or other activity of the target polynucleotide. An antisense nucleic acid can inhibit DNA replication or DNA transcription by, for example, interfering with the attachment of DNA or RNA polymerase to the promoter by binding to a transcriptional initiation site or a template. It can interfere with processing of mRNA, poly(A) addition to mRNA or translation of mRNA by, for example, binding to regions of the RNA transcript such as the ribosome binding site. It can promote inhibitory mechanisms of the cells, such as promoting RNA degradation via RNase action. The inhibitory polynucleotide can bind to the major groove of the duplex DNA to form a triple helical or "triplex" structure. Methods of inhibition using antisense polynucleotides therefore encompass a number of different approaches to altering expression of specific genes that operate by different mechanisms (see, e.g., Helene & Toulme, *Biochim. Biophys. Acta.*, 1049: 99–125 (1990)).

An "adenovirus" is a virus that is a member of the Adenoviridae family, e.g, adenovirus strain 5.

A "Dependovirus" is virus that is a member of the Dependovirus genus of the Parvoviridae family. For example, adeno-associated virus, or AAV, is a member of the Dependovirus genus.

A "togavirus" is a virus that is a member of the Togaviridae family and "Alphavirus", is a genus of the Togaviridae family. Members of the Alphavirus genus include, e.g., Semliki Forest Virus (SFV) and Sindbis Virus.

A "retrovirus" is a virus that is a member of the Retroviridae family. "Lentivirus" is a genus of the Retroviridae family, as is "Oncornavirus." Lentiviruses include, e.g., HIV-1 and HIV-2. Oncornaviruses, or "type C viruses" include murine viruses such as Moloney murine leukemia virus (Mo-MuLV), and murine leukemia virus (MuLV).

C. Construction of a Chimeric Primary Viral Genome

1. Components of Chimeric Primary and Secondary Viruses

A chimeric primary viral genome contains viral nucleic acid sequences from two different types of viruses. First, the chimeric primary viral genome includes nucleic acid sequences from a "primary" virus that can be packaged into a primary virus for infection of producer cells. Second, the chimeric viral genome includes nucleic acid sequences from a "secondary" virus. These sequences optionally encode packaging components that package a secondary viral genome to produce a secondary virus for infection of target cells. Third, the chimeric primary virus optionally includes a secondary viral genome that can either integrate into a target host cell after infection or produce an lytic infection (see, e.g. Fassati et al., *Retroviral Vectors*, in *Molecular and Cell Biology of Human Gene Therapeutics* pp. 1–19 (Dickson ed., 1995)). Fourth, this secondary viral genome optionally includes an expression cassette with a heterologous gene that is expressed in the target cells. Thus, once a chimeric primary viral genome is constructed, it is packaged into a chimeric primary virus and used to infect producer cells, in which the chimeric primary virus directs production of a secondary virus. The secondary virus is packaged in the producer cell and used to infect target cells. In one embodiment, the producer cells are packaging cells that complement the chimeric primary virus and provide some or all of the packaging components for the secondary virus. In this case, the chimeric primary virus typically encodes a viral genome. In another embodiment, the producer cell provides a secondary genome. In another embodiment, the chimeric primary virus produces both the secondary viral genome and secondary virus packaging components.

a. Primary Virus Sequences

Any primary virus can be used as the source for the primary viral genome in the chimeric primary virus. Preferably, the primary virus has a broad host range. Preferred primary viruses include, e.g., adenoviruses, vaccina viruses, and herpes simplex viruses (HSV). Particularly preferred primary virus nucleic acid sequences include those derived from the family Adenoviridae (White & Fenner, *Medical Virology* (4th ed., 1994)). One embodiment of the primary virus is a primary viral genome derived from the strain adenovirus 5 (for the sequence of ad 5, see Chroboczek et al., *Virology* 186: 280–285 (1992)).

Typically, the chimeric primary viral genome includes nucleic acid sequences that allow packaging of a chimeric primary viral genome into a primary virus for infection of a producer host cell. These sequences include any packaging signal required for packaging components to recognize and package the genome, e.g., nucleotide positions 0–400 of adenovirus. In addition, the sequences include any additional structural components necessary to produce a primary virus. For example, to produce a primary adenovirus containing heterologous sequences, homologous recombination is typically used to provide a packagable viral genome. Thus, a "transfer vector" containing the heterologous sequences of choice is created that is flanked by adenovirus sequences. These sequences are used to homologously recombine heterologous sequences of the transfer vector into a packagable adenoviral genome (see Example I). Such sequences can be determined by one of skill in the art.

Typically, the chimeric primary virus is replication deficient (it cannot produce additional primary virus) and lacks a gene required for replication or packaging. For example, adenoviral vectors usually have the E1A gene deleted from their genome. This gene is essential for viral replication and is complemented by the packaging cell line 293. Thus, a replication deficient chimeric primary viral genome is packaged after introduction of the viral genome into 293 cells. Other genes that are commonly deleted in adenovirus vectors are E1B and E3.

b. Secondary Virus Sequences

The chimeric primary viral genome includes secondary virus nucleic acid sequences that direct the production of the secondary virus, either independently, in combination with another chimeric primary virus, or in combination with a producer cell complements the chimeric primary virus. Such secondary virus sequences include genes encoding packaging components and a secondary viral genome, which may also be provided by the producer cell. Any virus can be used as the source for the required secondary virus sequences, e.g., lentiviruses, oncornaviruses, papillomaviruses, adenoviruses, and alphaviruses. Preferred secondary viruses include those derived from the family Retroviridae (White & Fenner, supra). One embodiment of a secondary virus is derived from amphotropic murine leukemia virus-related "type C" viruses that have been used extensively for gene transfer, e.g., Moloney murine leukemia virus (Mo-MuLV) (for the nucleotide sequence of Mo-MuLV, see, e.g., Shinnick et al., *Nature* 293: 43–548 (1981)). Other retroviruses as a source of secondary sequences include, e.g., monkey, cat, bird, and human retroviruses. Other preferred secondary viruses include those derived from the family Togaviridae, more preferably alphaviruses, e.g., Semliki Forest Virus (SFV) and Sindbis Virus (White & Fenner, supra; Liljestrom & Garoff, *Biotechnology* 9: 1356–1361 (1991)).

Genes encoding secondary virus packaging components are provided by the chimeric primary viral genome, e.g., the retroviral packaging components encoded by the genes gag, pol, and env. Alternatively, the packaging sequences can be provided by a complementary producer host cell. The secondary viral genome is provided either by the chimeric primary virus or by the producer host cell. The secondary viral genome includes any packaging signal required for packaging of the viral genome. For example, in one embodiment, a retroviral packaging signal ($\psi$) allows packaging of the retroviral genome into infectious viral particles. In addition, the viral genome may include a heterologous gene operably linked to a promoter, for expression in a target cell. In another embodiment, the secondary retroviral genome can also include, e.g., sequences from the 5' and 3' ends of the retroviral genome, including a retroviral promoter. These sequences can flank the heterologous gene in the retroviral genome and are used to regulate its transcription after provirus integration. These sequences are also involved in proviral production and integration. Other useful retrovirus sequences can be included in the retrovirus packaging cassette, by methods known to those skilled in the art. For example, human retroviruses such as HIV contain other accessory proteins and regulatory nucleic acid sequences In another embodiment, the secondary virus and viral genome are derived from an alphavirus, e.g., Semliki Forest virus (SFV) or Sindbis virus. The alphavirus sequences typically required for production of an secondary virus include genes that encode packaging components, e.g., C, p62, and E1. The viral genome typically includes the genes encoding replicase (NSP1–4) operably linked to a promoter, a genomic promoter, and a heterologous gene operably linked to a subgenomic promoter. The viral genome also includes a packaging signal. After the chimeric primary virus transduces the producer cell, replicase is produced. This protein then transcribes an RNA genome using the genomic promoter, which is packaged into an SFV particle and can be used to infect a target cell. Upon infection of a target cell, replicase is translated and transcribes an "auto-catalytic" expression cassette using the subgenomic promoter.

The secondary virus is capable of either producing a lytic infection, e.g., SFV, or integrating the secondary viral genome into the DNA of the target host cell, e.g, Mo-MuLV. Upon production of a lytic infection, a heterologous gene is often transiently expressed at high levels. Integration allows constitutive or inducible expression of a heterologous gene.

The secondary virus components and genome can be provided by a single chimeric primary virus, or the sequences can be provided by two or more viruses that complement each other in trans. The secondary viral genome can also be provided by the producer host cell. In addition, secondary virus packaging components can be provided by packaging cells in trans that complement the chimeric primary virus. Secondary viruses produced by complementary producer cells are typically present in very high titers in the producer cell supernatant.

c. Expression Cassette Sequences

The secondary viral genome can include an expression cassette, containing a heterologous gene or nucleic acid sequence. Typically, the heterologous gene will confer a therapeutic benefit to the host cell. The heterologous gene can be transcribed in host cells after infection with the secondary virus, during either a lytic infection or after integration of the provirus into the host cell genome (see Fassati et al., supra). Transcription of the heterologous gene can be regulated by viral or cellular promoters.

A typical expression cassette contains a promoter operably linked to the nucleic acid sequence encoding the protein. The promoter used to direct expression of the heterologous gene or nucleic acid depends on the particular application. The promoter is preferably positioned about the same distance from the heterologous transcription start site as it is from the transcription start site in its natural setting. As is known in the art, however, some variation in this distance can be accommodated without loss of promoter function. Often the promoter used to drive the heterologous gene is a retrovirus promoter from the LTR region. Other promoters include any promoter suitable for driving the expression of a heterologous gene in a host cell, including those typically used in standard retrovirus vectors, e.g., SV40 and CMV promoters.

Polyadenylation sequences are also commonly added to the retrovirus packaging cassette. Termination and polyadenylation signals that are suitable for the present invention include those derived from retrovirus LTR sequences. Other suitable sequences include polyadenylation and termination sequences derived from SV40, or a partial genomic copy of a gene already resident on the expression vector.

The expression cassette optimally includes enhancer elements that can stimulate transcription up to 1,000 fold from linked homologous or heterologous promoters. Many enhancer elements derived from viruses have a broad host range and are active in a variety of tissues. The retroviral U3 region enhancer, the SV40 early gene enhancer, polyoma virus enhancer, and human or murine cytomegalovirus enhancer are all suitable for inclusion in an expression cassette (see *Enhancers and Eukaryotic Expression* (1983)).

In one embodiment, the expression cassette is an autocatalytic expression cassette that encodes replicase and contains a heterologous gene operably linked to an alphavirus subgenomic promoter. The replicase provides high levels of expression from the subgenomic promoter. Suitable replicase genes and subgenomic promoters include, e.g., those derived from Sindbis virus and SFV.

Any heterologous nucleic acid that is suitable for introduction into a host cell can be used in the present invention by one skilled in the art. Genes useful for gene therapy can be introduced into mammals using the methods and viruses of this invention. Genes encoding enzymes, hormones, ribozymes, antisense RNA, viral inhibitors, ion channel proteins such as CFTR, and blood proteins such as Factor IX are examples of heterologous nucleic acids useful in gene therapy. Genes encoding selectable markers, such as those that confer antibiotic resistance, can be used to detect and isolate cells infected with the chimeric primary or secondary virus.

A functional heterologous gene can be used to functionally replace a mutated gene in a mammal using gene therapy. For example, the gene encoding human clotting factor IX can be used to treat hemophilia B and the gene encoding CFTR can be used to treat cystic fibrosis. Another embodiment of a heterologous nucleic acid used in gene therapy is a ribozyme, which can specifically target and cleave another RNA in the host-cell. Yet another embodiment is an antisense nucleic acid.

2. How to Construct and Package a Chimeric Primary Virus and Produce Secondary Virus The previous section described the components of a chimeric primary virus. The next step is to construct and package a chimeric primary virus for infection of producer host cells and production of secondary virus. A chimeric primary viral genome is prepared by first isolating the constituent nucleic acids. The nucleic acids are then joined, for example, using restriction endonuclease sites at the ends of the molecule. The recombinant molecule is ligated into suitable a plasmid or vector. Methods for preparing a recombinant nucleic acid are know by those skilled in the art (see Sambrook et al., *Molecular Cloning. A Laboratory Manual* (2d ed. 1989); Ausubel et al., *Current Protocols in Molecular Biology* (1995)).

One preferred method for obtaining specific nucleic acids combines the use of synthetic oligonucleotide primers with polymerase extension on a MRNA or DNA template. This PCR method amplifies the desired nucleotide sequence (see also U.S. Pat. Nos. 4,683,195 and 4,683,202). Restriction endonuclease sites can be incorporated into the primers. Genes amplified by PCR can be purified from agarose gels and ligated together. Alterations in the natural gene sequence can be introduced by techniques such as in vitro mutagenesis and PCR using primers that have been designed to incorporate appropriate mutations. Another preferred method uses known restriction endonuclease sites to isolate nucleic acid fragments from DNA plasmids.

In one embodiment, chimeric primary viral genomes are constructed using "transfer vectors" and homologous recombination. This method is useful when a viral genome is too large to efficiently manipulate with restriction enzymes and ligation. Instead, a smaller transfer vector is prepared that contains the chimeric primary viral genome sequences of choice. This vector is then homologously recombined with a viral genome. The recombinant viral genome thus contains the chimeric sequences of interest. For example, chimeric adenovirus genome is made in this manner using co-transfection of a transfer vector with the plasmid pJM17 (see Example I). Typically, the homologous recombination event occurs in a packaging cell. The recombinant virus containing the chimeric sequences of choice is packagable based on size, whereas the non-recombinant genome lacks a packaging signal or is too big to be packages. Once the recombinant genome containing the chimeric sequences is generated, it is packaged by the cell into a chimeric primary virus.

If necessary, the chimeric primary virus is packaged by any means suitable in the art (see Sambrook, supra, Ausubel, supra). A commonly used transcomplementing cell line for packaging retrovirus is PA317 (Miller & Buttimore, *Mol.*  *Cell. Biol.* 6: 2895–2902 (1986)). A commonly used transcomplementing cell line for packaging adenovirus is the transformed primary human embryonal kidney cell line 293 (Roizman, *Proc. Natl. Acad Sci USA* 93: 11307–11312 (1996)). Vaccinia virus does not require a transcomplementing cell line for packaging. A vector encoding a chimeric primary viral genome is typically introduced into packaging cells by standard methodology, e.g., transfection, electroporation and the like. In one embodiment, chimeric primary viral sequences are cotransfected into 293 cells with pJM17 to produce a chimeric viral genome, which is then packaged into infectious chimeric primary virus.

The chimeric primary virus particles are collected and used to infect a producer cell by standard methodology (see Sambrook, supra, Ausubel, supra). In one embodiment, the producer cell is also a retroviral packaging cell line. Generally, after infection with the chimeric primary virus, producer cells are incubated under standard cell culture conditions to allow packaging of the secondary virus genome and budding of viral particles into the cell supernatant. The cell supernatant is then collected after a suitable amount of time, e.g., after 24 hours. The supernatant is then frozen or used immediately. In this way, the infected cell becomes a producer host cell for the secondary virus.

Infectious secondary virus particles are shed from the producer host cell, and are capable of subsequently infecting target host cells using standard methodology. The secondary viruses producing either a lytic infection or integrate into the DNA of the target host cell. Often the secondary virus is replication deficient.

D. Rescue of Unknown Viral Genomes From Host Cells

The chimeric primary viruses described above have many uses. One such use is to "rescue" unknown viral genomes from cells. An unknown viral genome is "rescued" when the chimeric primary virus provides packaging components in trans that recognize and package the unknown genome into a secondary virus particle. The chimeric primary viruses, e.g., adenoviruses, vaccina viruses and herpes viruses have the ability to rescue some or all of the genomes of other viruses, e.g., lentiviruses, oncornaviruses, papillomaviruses, adenoviruses, and alphaviruses. Such unknown viruses may be capable of inducing disease, and such chimeric primary viruses are used in diagnostic or exploratory procedures to rescue and to identify disease causing viral agents in tissues. Furthermore, it may be possible to identify new viruses that are transmissible among humans for use as vectors for gene therapy.

No human retroviruses of the genus Oncornavirus have been identified. However, there have been reports of type C retrovirus particles in micrographs of human milk and the possibility exists that human disease could result from the infectious transmission of oncornaviridae retroviruses (Wilkinson et al., supra). Lentiviruses are known to infect humans. Rescue of retrovirus genomes with chimeric adenoretroviruses thus has a diagnostic application.

Many cell types are suitable for the creation of a packaging cell line, for example, HeLa cells and NIH 3T3 cells, from which unknown viruses can be rescued. The host scope of the packaging cell line may also be varied. In the preferred embodiment of the present invention, the packaging cell line produces viral particles that can infect human cells. Suitable methods know to those skilled in the art are used to harvest the packaged rescued virus from the packaging cell lines, as described above (see generally Bunnell & Morgan, *Retrovirus-Mediated Gene Transfer*, in *Viral Genome Methods*, pp. 3–23 (Adolph ed., 1996)).

The biological activity of the rescued viral particles can be tested by infecting any suitable cell type and examining viral replication and/or integration. Cells are infected after titering virus-containing cell supernatants according to standard methods (see, e.g., Bunnell & Morgan, supra).

The rescued viral particles can also be directly analyzed, e.g, with cDNA synthesis using the rescued genomes as template and/or amplification of the rescued genome with PCR, followed by sequencing of the rescued genome. Viral genomes can be characterized by any of a number of means well known to those of skill in the art. These methods include the detection of specific polynucleotide by well known methods such as Southern analysis, northern analysis, dot blot analysis, gel electrophoresis, PCR, and RNase protection assays.

In one embodiment, chimeric primary adeno-retroviruses provide a means to efficiently infect cells with an adenovirus or a group of adenoviruses that minimally encode retroviral gag, pol, and env genes (see Example VI) . These genes encode the proteins necessary to package a transcribed retroviral RNA genome that contains a packaging signal ($\psi$). The packaged and secreted retrovirus particles that result from the transduction of cells with the adeno gag-pol-env chimera would only contain "rescued" RNA retroviral genomes.

In this embodiment, the rescued viral genomes are analyzed by a number of methods. The rescued retroviral particles are used to subsequently infect a host cell, e.g., one that provides packaging components for further production of the rescued virus particle (see Miller, *Hum. Gene Ther.* 1: 5–14 (1990)). Typically, packaging cells produces in trans the proteins necessary for formation of a viral particle. However, the packaging cells do not themselves produce packagable retrovirus RNA genomes because they contain retrovirus sequences from which the $\psi$ site has been deleted. Thus, rescued, replication deficient retrovirus RNA genomes can be propagated using packaging cell lines.

E. Production of Non-human Transgenic Animals

Another important use of the chimeric primary viruses is for the production of nonhuman transgenic animals. The chimeric primary viruses provide secondary viruses that carry a heterologous gene that confers a beneficial phenotype to the host mammal. One previous difficulty associated with transgenic non-human animals is the number of offspring that must be analyzed for identification of an animal that carries the appropriate transgene. In addition, often the heterologous transgene is not present in viable oocytes or spermatocytes because the transgenic animal is a chimera that is unable to pass the heterologous gene to its offspring. The use of the chimeric primary virus system provides an highly efficient method to create transgenic gametes and embryos.

Suitable non-human animals include transgenic mice, transgenic pigs, transgenic sheep, transgenic rabbits, transgenic cattle, transgenic rats, and other mammalian non-human species amenable to transgenesis by methods known in the art (see, e.g., Houdebine, *J. Biotechnology* 34: 296–287 (1994)). Transgenic non-human animals can be made according to standard techniques. Typically, gametes are isolated and fertilized in vitro, and then implanted into the uterus of the surrogate female animal for subsequent development. Such gametes can be infected with a chimeric primary virus before or after fertilization. The chimeric primary virus, which direct production of a secondary virus that contains a heterologous gene, are described above. The embryo produced by in vitro fertilization is thus a producer cell for secondary virus, which subsequently infects other cells of the embryo. Suitable heterologous genes include therapeutic genes that treat a disease state as discussed below, or genes that confer increased commercial desirability to the animal.

In addition to the techniques for producing transgenic animals described above, chimeric primary virus can be injected into the sperm producing organs of an adult animal. The infected sperm cells would then serve as producer host cells, for subsequent infection of target sperm cells with the secondary virus. The secondary virus can include a selectable marker that is used to isolate the sperm transduced by the secondary virus. Such selectable markers include, e.g., the *Aeqorea victolia* green fluorescent protein (GFP) (Prasher et al., *Gene* 111: 229–233 (1992)), which would permit selection of transgene expressing sperm by FACS sorting. Another suitable marker is a cell surface marker such as a defective nerve growth factor receptor which would permit the isolation of transgene expressing sperm by affinity chromatography or a variation thereof.

In one embodiment, the selectable marker can be a gene that restores sperm viability. Animals with defined defects that lower the viability of their sperm (e.g., the equivalent of immotile cilia or cystic fibrosis) can be identified. The secondary virus produced by the chimeric primary virus would include a transgene of interest (e.g., Factor IX) and a selectable marker that restores viability to the spermatozoa.

F. Ex Vivo and In Vivo Gene Therapy

The chimeric primary viruses of the invention can be also used for mammalian gene therapy, preferably for human gene therapy. Gene therapy provides methods for combating chronic infectious diseases such as HIV infection, as well as non-infectious diseases such as cancer and birth defects (see generally Anderson, *Science* 256: 808–813 (1992); Yu et al., *Gene Ther.* 1: 13–26 (1994)). Gene therapy can be used to transduce cells with either an ex vivo or an in vivo procedure.

One advantage of this system is that the combination of the chimeric primary and secondary virus provide an efficient means of diffusing the gene therapy vector throughout a cell population. Target cells that are infected in vitro are infected efficiently using this system because the producer cells provide high titers of secondary virus. For example, producer cells that complement the chimeric primary virus produce very high titers of secondary virus. Target cells are infected more efficiently in vivo because the combination of the vectors provide a wider path of diffusion standard methods such as injection. Another advantage of the system is that autologous producer and target cells can be used to alleviate immune response to the gene therapy vector.

1. Immune Response

The chimeric primary viruses can be used in vivo to direct the synthesis of large quantities of secondary virus, e.g., retrovirus, in which the membrane constituents are derived from the cells of the patient (human or animal) and are therefore autologous. This feature eliminates the possibility that an immune response to the membrane constituents of the virus preparation will inactivate the secondary virus. This inactivation, due to a xenogeneic or allogeneic immune response, can also be avoided when syngeneic or autologous cells are used as the virus producer cells in vitro. The ability to directly create these "autologous" virus producer cells in vivo and ex vivo is an important use of this technology in medical applications. In addition, the chimeric primary viruses of the invention can be used to infect cells that have been matched via haplotype to the individual who is to receive them, or to infect mismatched cells that have been irradiated.

The producer host cells transduced by the chimeric primary viruses direct the synthesis and release of the "secondary" virus that transduce the adjacent target host cell tissues. The immune system will eventually lead to the removal of the cells transduced with the chimeric primary virus, e.g., adenovirus, but the target cells transduced with the secondary virus, e.g., retrovirus, will persist indefinitely, resulting in curative gene therapy.

2. Therapeutic Methods

The chimeric primary viruses produce secondary viruses that confer a therapeutic benefit to the target host cell. Often the secondary virus carries a heterologous gene or nucleic acid that produces this effect. The secondary viruses are capable of producing a lytic infection or an integrative event. Generally, integrative secondary viruses are used for long term treatment, and lytic secondary viruses are used for transient or anti-proliferative treatments. Integrative viruses can be used to provide functional genes to cells that contain defective copies. They can be used as anti-proliferative therapeutics by providing antisense nucleic acids. They can be used to alter transdominant mutations by providing an antisense molecule for the defective gene.

Secondary viruses that produce a lytic infection, e.g., Semliki Forest virus, can be used to treat a disease condition such as cancer, viral infection, or another proliferative disease that can be treated by transient expression of a gene or cell lysis. In addition, certain conditions such a secondary virus can provide short term therapy for a disease such as a bleeding disorder, by providing a clotting factor when necessary. The secondary viruses that produce a lytic infection typically result in production of large amounts of the heterologous gene of choice. Such secondary viruses can be targeted to specific target cells as described below, such as cancer cells, for infection and subsequent lysis of the target cells. This virus may contain a heterologous gene that is transiently expressed in high amounts. When the target cell lyses, an "oncolysate" may be formed that contains a heterologous protein expressed by the secondary virus, such as a cytokine. The oncolysate is used to induce tumor rejection. The lytic infection itself may also be used as a means to kill specifically targeted cells, as described below.

Any heterologous genes or transcription units suitable for gene therapy can be expressed by the secondary virus. Some conditions treated by gene therapy are chronic or congenital diseases that preferably treated by integration of a functional gene into the appropriate cell, e.g., hormones, cell receptors, and enzymes. In one embodiment of the invention, genes encoding proteins such as Factor IX and CFTR are used for gene therapy. Other disease conditions can be treated by killing the cell responsible for the disease condition, such as a cancer cell or a virally infected cell, e.g., an HIV infected cell. For example, suitable therapeutics can target RNAs (e.g., using ribozymes or antisense RNA), proteins (RNA decoys, transdominant proteins, intracellular single chain antibodies, soluble CD4), infectible cells (suicide genes), or the immune system (in vivo immunization).

3. Specific Targeting

Secondary viruses of this system can be constructed that are selectively targeted to target host cells. For example, secondary viruses can be constructed that allow preferential targeting of the tissue "stem cells," the self-renewing population of cells which serve as the source of the terminally differentiated cells. Examples of such tissues include skin, blood, and airway epithelium. Selective targeting is accomplished, e.g., via the retroviral env gene, which acts as the ligand for the target cell viral receptor. For example, pseudotyping the env gene of a retrovirus is used to alter the tropism of the virus particle. Amphotropic murine leukemia virus (ampho MuLV) env shows few trophic specificities whereas gibbon ape leukemia virus (GALV) env has much higher transduction efficiencies for mature T-lymphocytes. Amphotropic env can be used to target CD34 cells (Bunnell et al., *Blood* 89: 1987–1995 (1997)). Such targeting would provide an efficient means of gene therapy, since the stem cells containing the heterologous gene of choice would provide populations of differentiated cells that also contained this gene. In addition, if the secondary virus conferred a biologically selectable advantage, e.g., better growth or resistance to toxins, repopulation of the target organ with genetically altered cells could proceed more completely and more rapidly.

4. Ex Vivo Methods

Ex vivo methods for gene therapy involve transducing the cell ex vivo with a virus of this invention, and introducing the cell into the organism. The cells can be hematopoietic stem cells isolated from bone marrow or other cells that are in the host range of the packaged retrovirus particles of the invention. T cells are used in some embodiments in ex vivo procedures.

The same targeting strategy described above can be applied to the ex vivo transduction of cells, followed by re-infusion into a patient. For example, human umbilical vein endothelial cells can be transduced with a chimeric primary virus. These cells are then used as feeder cells supporting the growth of CD34 positive stem cells. These cells are also used as producer cells that provide secondary virus to the target CD34 cells. The CD34 positive stem cells would be cultured in the presence of a steady supply of secondary virus, prior to reintroduction into a patient. This strategy can be applied by one of skill in the art to any suitable tissue.

Several techniques are known for isolating T cells (see, e.g., Leavitt et al., *Hum. Gene Ther.* 5: 1115–1120 (1994)). The expression of surface markers facilitates identification and purification of T cells. Methods of identification and isolation of T cells include FACS, incubation in flasks with fixed antibodies which bind the particular cell type and panning with magnetic beads.

Stem cells are isolated from mammals for transduction and differentiation using known methods. Stem cells are isolated from bone marrow cells by panning the bone marrow cells with antibodies which bind unwanted cells, such as $CD4^+$ and $CD8^+$ (T cells), $CD45^+$ (panB cells), GR-1 (granulocytes), and $Ia^d$ (differentiated antigen presenting cell) (see Inaba et al., *J. Exp. Med.* 176: 1693–1702 (1992)).

In humans, hematopoietic stem cells can be obtained from a variety of sources including cord blood, bone marrow, and mobilized peripheral blood. Purification of CD34+ cells can be accomplished by antibody affinity procedures (see Ho et al., *Stem Cells* 13 (suppl. 3): 100–105 (1995); see also Brenner, *J. Hematotherapy* 2: 7–17 (1993)). Cells can also be isolated and cultured from patients. Alternatively, the cells used for ex vivo procedures can be those stored in a cell bank (e.g., a blood bank). The advantage to using stem cells is that they can be differentiated into other cell types in vitro, or can be introduced into a mammal (such as the donor of the cells) where they will engraft in the bone marrow. Methods for differentiating bone marrow cells in vitro into clinically important immune cell types using cytokines such a GM-CSF, IFN-γ and TNF-γ are known (see, e.g., Inaba et al., supra).

One embodiment of the invention that is useful for ex vivo methods is the use of chimeric primary viruses and producer cells that complement the chimeric primary virus to produce secondary virus. The use of producer cells that provide secondary virus packaging components provide high titers of secondary virus supernatant and efficient infection of target cells.

5. Administration

Chimeric primary viruses (for in vivo gene therapy) and transduced producer host cells or transduced target cells (for ex vivo gene therapy) can be administered directly to a patient, preferably a human. Administration is by any of the routes normally used for introducing a molecule or cell into ultimate contact with blood or tissue cells. The viruses of the invention are administered in any suitable manner, preferably with pharmaceutically acceptable carriers. Suitable methods of administering such viral vectors in the context of the present invention to a patient are known to those skilled in the art.

Pharmaceutically acceptable excipients are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration and intravenous administration are suitable methods of administration.

The dose administered to a patient, in the context of the present invention should be sufficient to effect a beneficial therapeutic response in the patient over time. The dose will be determined by the efficacy of the particular heterologous gene in the expression cassette and the condition of the patient, as well as the body weight or surface area of the patient to be treated. The size of the dose also will be determined by the existence, nature, and extent of any adverse side-effects that accompany the administration of a particular virus or transduced cell type in a particular patient.

For administration, viruses and transduced cells of the present invention can be administered at a rate determined by the transduced cell type, and the side-effects of the virus or cell type at various concentrations, as applied to the mass and overall health of the patient. Administration can be accomplished via single or divided doses. For a typical 70 kg patient, a dose equivalent to approximately 0.1 $\mu$g to 10 mg are administered. Transduced cells are optionally prepared for reinfusion according to established methods (see, e.g., Abrahamsen et al., *J. Clin. Apheresis* 6: 48–53 (1991); Carter et al., *J. Clin. Apheresis* 4: 113–117 (1988); and Aebersold et al., *J. Immunol. Methods* 112: 1–7 (1988)).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Construction and Packaging of a Chimeric Primary Adenovirus-retrovirus, AVLSXIN

1. Construction of the Chimeric Primary Viral Genome

To produce a chimeric primary virus, adenovirus was chosen as the source of the primary virus and a retrovirus was chosen as the source of the secondary virus. The plasmid pAVC2, which contains adenovirus sequences, was used to construct the chimeric primary virus. This plasmid has a pBluescript SK+ (Stratagene) backbone and the following components: (1) nucleotide base positions 0–400 from adenovirus strain 5; (2) an expression cassette containing the CMV promoter, a multiple cloning site, SV40 intron, and a polyadenylation signal; and (3) an additional 2.9 kb of adenovirus 5 DNA (positions 3328–6200). These adenovirus sequences provided essential structural elements for packaging a viral genome into an adenovirus particle. Nucleotide base sequences 0–400 permit packaging, and the additional 2.9 kb permit recombination with a complementary plasmid to reconstitute the adenovirus genome, e.g., pJM17.

The source of the retrovirus was the plasmid LXSN. pLXSN contains the 5' LTR, a packaging signal ($\psi$), a multiple cloning site, an SV40 promoter, and the neo gene (Miller & Rossman, *Biotechnology* 7: 980 (1989)). The expression cassette was deleted from pAVC2, and the provirus of LXSN, derived from the retrovirus Moloney murine leukemia virus (Mo-MuLV) was inserted in its place using standard bacterial cloning procedures (see, e.g., Ausubel, supra; Sambrook, supra). The resulting plasmid (pAVLXSN) contains, in the following order, nucleotide base positions 0–400 from adenovirus 5, LXSN (with the 5' LTR adjacent to adenovirus nucleotide base position 400), and an additional 2.9 kb of adenovirus 5 DNA (positions 3328–6200).

2. Recombination and Packaging of a Chimeric Primary Virus

A chimeric adenovirus genome was created by homologous recombination of pAVLXSN with a plasmid that provided the remainder of the adenovirus genome. For this experiment, the plasmid pJM17 provided the remainder of the genome (Prevec & Graham, *Biotechnology* 20: 363–390 (1992)). In pJM17, the E1 gene, which is essential for replication, has been disrupted with a large piece of DNA. Any recombinant adenoviruses that retain this disrupted E1A cannot be packaged, since they are too large. However, recombinants that contain the LXSN retroviral sequences in place of the large piece of DNA can be packaged, since they are smaller. These chimeric adenoviruses still lack the E1A gene, and are packaged by complementation of the E1A gene by packaging cells, e.g., 293 cells.

The plasmid AVLXSN, described above, was therefore co-transfected with the plasmid pJM17 into 293 packaging cells by calcium phosphate co-precipitation. In the cell, the plasmids recombined to produce packagable, chimeric adeno-retrovirus. The chimeric primary viral genome is then packaged into an adenovirus particle. The chimeric primary adeno-retrovirus, designated AVLXSN, was subsequently isolated and purified by standard techniques.

Example II

Infection of Producer Cells With Chimeric Primary Virus AVLSXN, Production of Secondary Virus, and Infection of Target Cells 1. Infection of FLYA13 Producer Host Cells With Chimeric Primary Virus and Infection of Target Cells With Secondary Virus The chimeric primary virus AVLXSN was tested for its ability to direct the production of secondary retrovirus in a producer host cell and subsequently infect target cells. This particular chimeric primary virus lacks the gag, pol, and env genes, which are necessary to independently direct the production of secondary virus. Therefore, retroviral packaging cells that can complement this function were chosen as the producer cells. However, the system of the invention also provides chimeric primary viruses, which contain all the components necessary to direct production of secondary virus, with the secondary viral genome provided either by the chimeric primary virus or by the producer host cell.

FLYA13 retrovirus packaging cells were selected as complementary producer cells. These cells are a packaging cell line derived from human cells that produces amphotropic retrovirus particles (virus particles that are able to infect murine and non-murine cells, including human cells). AVLSXN chimeric primary virus was used to infect the FLYA13 cells. AVLSXN includes a retroviral genome (the secondary viral genome) that encodes the neo gene linked to a promoter. Because neo gene is transcribed from the retroviral genome during production of the secondary virus, therefore, the producer cells should become neo resistant.

After the FLYA13 cells were transduced with AVLSXN, they were selected for neo gene expression with G418. Approximately 400 G418 resistant colonies were isolated. When control virus lacking the retroviral sequences was used, no resistant colonies were isolated. This result established that the LXSN secondary viral genome was transcriptionally active in these packaging cells.

Furthermore, the LXSN secondary retroviral genome was packaged in the producer cell to produce infectious viral particles, which were used to infect target 9L cells. After the producer cells were infected with the chimeric primary virus, cell supernatant containing secondary virus was collected. The supernatant was frozen, thawed, and filtered. The supernatant containing the secondary virus was then used to transduce the target rat glioma 9L cells by standard techniques.

After the secondary virus infects the target cell, the secondary genome integrates as a provirus into the target cell genome, and the neo gene is transcribed. The secondary virus should therefore confer neo resistance to the target host cells. Transduced 9L cells were selected for presence of functional retroviral provirus. The neo selection demonstrated that the retroviral titer of the producer cell supernatant was roughly one million retroviral particles per ml. Thus, the FLYA13 producer cells directed production of secondary virus that was able to infect target 9L cells.

The experimental controls include the use of adenovirus expressing the E. coli β-galactosidase gene instead of the retrovirus genome. When the control virus was used to transduce FLYA13 cells, the supernatant did not confer resistance to neomycin. Further, the control supernatant media did not confer long term expression of the β-galactosidase gene.

2. Infection of PA317 Producer Host Cells With Chimeric Primary Virus and Infection of Target Cells With Secondary Virus As described above, the chimeric primary virus AVLXSN was used to transduce a second line of producer cells, which made secondary virus that subsequently infected target cells. In this experiment, PA317 packaging cells were used as the producer cells. Upon infection with the chimeric primary virus, the PA317 cells exhibited neo resistance, as described above for the FLYA13 cells. After the producer cells were infected, cell supernatant containing secondary virus was collected, as described above for the FLYA13 cells. The supernatant was then used to infect target 9L cells, with similar results, e.g., the secondary viral genome conferred neo resistance to the target host cells. Similar experiments were conducted using three additional packaging cell lines. Similar results were obtained under all conditions.

Example III
Characterization of the Secondary Viral Genome Integrated in Target Cells The 9L target cells described above in Example II, which were infected with secondary virus, were analyzed for the presence of the secondary virus genome. 9L cells that were transduced by the producer cell supernatant derived from the AVLXSN-transduced FLYA13 cells were amplified in culture. DNA was isolated from these cells, digested with XbaI, and then electrophoresed and subjected to Southern analysis. The blot was hybridized to a probe specific for LXSN. In particular, the hybridization pattern was characteristic of proviral integration into the 9L cell chromosomes. This pattern indicates that the LXSN sequences have integrated via the normal retroviral pathway.

Example IV
Construction of an Independent Chimeric Adeno-retrovirus

A chimeric primary virus is constructed as described above in Example I, with the following changes. The chimeric primary virus contains all packaging (gag, pol, and env) and genomic secondary virus sequences (e.g., 5'LTR, ψ) so that it is genetically competent to direct production of a secondary virus, without additional constructs or virus. Thus, non-packaging cell lines are substituted as producer cell lines for the packaging cell lines described in Example II.

Example V
Construction of a Chimeric Adenovirus-SFV Virus

A chimeric primary adeno-SFV is constructed as described above in Example I, except that sequences of the Semliki Forest Virus (SFV) genome derived from plasmid pSFV1 are substituted for LSXN (see Liljestrom & Garoff, supra); Ausubel, supra). The essential SFV sequences are an autocatalytic expression cassette that contains the NSP1–4 genes encoding replicase, operably linked to a promoter, and a heterologous gene operably linked to the SFV subgenomic promoter, which is recognized by replicase. Replicase is translated, and then it recognizes the subgenomic promoter and transcribes the heterologous gene operably linked to this promoter. The subgenomic promoter and replicase provide high amounts of expression.

The chimeric primary adeno-SFV is packaged in 293 cells as described above in Example I, and used to infect a suitable producer cell line such as BHK-21 cells (Ausubel, supra). Production of a lytic infection is observed by examining expression of a suitable heterologous protein expressed by the SFV genome (which contains the autocatalytic expression cassette). Alternatively, the SFV genome can contain wild type SFV sequences, and the infection can be monitored by examining cell lysis.

Example VI
Construction of a Chimeric Adenovirus for Rescuing Retroviral Genomes 1. Construction of the Chimeric Primary Viral Genome, and Packaging of the Chimeric Primary Virus A chimeric primary virus was constructed for use in rescuing an unknown secondary viral genome from a producer cell. An adenovirus that contains a retroviral envelope protein gene was constructed as described in Example I. The resulting chimeric primary virus was called AVC2.env. This chimeric primary virus lacks a secondary viral genome. The envelope protein was from an amphotropic strain of MuLV (see Ott et al., J. Virol. 64: 757–766 (1990)). The chimeric adenovirus was packaged as described above in Example I.

2. Infection of Producer Cells

This chimeric primary virus (AVC2.env) was used to transduce a cell line that has an integrated copy of the retrovirus LNL6 (which contains a neo resistance marker). LNL6 serves as the secondary viral genome that is packaged by the chimeric primary virus into secondary virus.

Because the chimeric primary virus contains only one packaging component, the env gene, the remaining packaging components were provided by an expression cassette that has been integrated into the DNA of the producer host cell. This expression cassette expresses retroviral gag and pol products. In other embodiments of the invention, the chimeric primary virus provides all the packaging components necessary to package a secondary viral genome and produce secondary virus.

These packaging cells thus act as the producer cells and were used to transcomplement the env gene provided by the chimeric primary virus AVC2.env by providing gag, pol, and a retroviral genome. The producer cells were transduced with either AVC2.env or AV.lacz4 (a control virus containing the β-galactosidase gene).

3. Infection of Target Cells

Secondary virus was collected and analyzed for rescue of the LNL6 retroviral genome. Supernatant was harvested from the producer cells at 48 hrs and used to transduce target 9L cells as described in Example II. Transduced 9L cells were selected in G418 containing media and resistant colonies amplified and tested by Southern blot as described in Example III. Rescue and packaging of the LNL6 retroviral genome was verified in this manner.

4. Construction of a Transcomplementing Chimeric Primary Virus

An adenovirus that expresses retroviral gag and pol genes was constructed as described above in Example I. This chimeric primary virus was used in combination with the chimeric primary AVC2.env virus to rescue the LNL6 retroviral genome from 9L cells, as described above. In this manner, the chimeric primary viruses act collectively to rescue the secondary viral genome and produce secondary virus. No packaging cells were used as the producer cells since the chimeric viruses encode all the necessary components to package the rescued secondary viral genome.

Example VII
Transcomplementation and Production of Secondary Retrovirus With Amphotropic, Ecotropic, Gibbon-ape, and Cat Envelope Proteins The primary adenovirus AV-LXSN was used to transduce 5 different retroviral packaging cell lines (PA317, FLYA13, GP+E 86, PG13, and FLYRD18). In these cell lines, LXSN retrovirus was produced with either amphotropic, ecotropic, gibbon-ape leukemia virus or cat endogenous virus derived envelopes. Envelope specific tropism was confirmed in three target cell types (mouse NIH-3T3 cells, rat 9L gliosarcoma cells, and human TE671 cells). PG13, GP+E 86, FLYA13 and FLYRD18 cell lines produced retroviral titers (G418$^R$ cfu/ml) comparable with those produced by standard techniques (maximum titers in TE671 cells: PG13 $4.5\times10^5$ cfu/ml, FLYA13 $3.5\times10^7$ cfu/ml, FLYRD18 $8.5\times10^6$ cfu/ml; maximum titer in NIH-3T3 cells: GP+E 86 $3\times10^6$ cfu/ml). Retrovirus could be detected in supernatants within 24 hours of AV-LXSN transduction and persisted for at least 120 hours. No replication competent retrovirus or adenovirus was detected. Southern blot analysis of genomic DNA purified from populations of G418$^R$ cells showed the presence of a 2.7 kb Xba I fragment containing the G418$^R$ gene. This fragment could be generated only by reverse transcription of AV-LXSN to produce LXSN retroviral vector.

Example VIII
Transduction of Animals In Vivo With Secondary Retrovirus

The adenoviral-based chimeric vector system described above was used to generate a secondary retrovirus in the liver cell lines HepG2 and HUH7, the intestinal and respiratory epithelial cell lines IEC18 and 16HBE14o- in vitro, and in rat glioma 9L cells in vitro and in vivo. The chimeric virus system consisted of a series of adenoviruses (constructed as described above) encoding: (1) MoMLV gag.pol (Axtet-gag.pol); (2) the VSV-G retroviral envelope (Axtet-VSVG; (3) the provirus LXSN expressing the neomycin phosphotransferase (neo) gene (AVLSXN); and a transcriptional regulator to control expression of gag.pol and envelope (AVrtTA or AxCA-NtTA). The titers of the retroviral supernatants generated by co-transduction of cells with different combinations of these adenoviruses are shown below.

TABLE I

| | Adenoviruses | | | | Hep-G2 | HUH 7 | IEC1 8 | 16HB E14o- | 9L |
|---|---|---|---|---|---|---|---|---|---|
| AV-LXSN | Axtet-VSVG | Axtet-Gag.pol | AV-rtTA | AxCA-NtTA | \multicolumn{5}{l}{Retroviral titer cfu/ml (G418$^R$)} | | | | |
| 5 | 5 | 5 | 5 | — | $2 \times 10^5$ | $1 \times 10^2$ | $2 \times 10^3$ | $2 \times 10^2$ | $3 \times 10^1$ |
| 5 | 5 | 5 | — | 5 | $6 \times 10^4$ | $3 \times 10^1$ | $1 \times 10^2$ | $1 \times 10^2$ | $3 \times 10^3$ |
| 5 | — | — | — | — | $1 \times 10^1$ | 0 | 0 | 0 | 0 |

In vivo, cohorts of animals received either AV-LXSN alone, or AV-LXSN, Axtet-VSVG, Axtet-Gag.pol and AVrtTA, ±doxycycline. Virus was administered intratumorally into a subcutaneous 9L rat tumor model. Only cells harvested from tumors transduced with all of the transcomplementing viruses showed expression of G418$^R$. All G418$^R$ cells generated in vitro by transduction using the full complement of transcomplementing viruses demonstrated the presence of integrated proviral LXSN DNA. In vivo, transduction combined with doxycycline induction of gag.pol and VSV-G lead to typical retroviral integration into chromosomal DNA, however, in the absence of doxycycline induction, integration was either aberrant or LXSN DNA was carried episomally.

Example IX
Rescue of Integrated Retroviral Genomes in Human and Rat Cells

Chromosomally embedded, replication-incompetent retroviruses were efficiently rescued using the chimeric virus system described above. The model system for viral rescue was embedded, replication-deficient murine Type C oncornaviruses lacking functional gag.pol and env genes. In this system, a chromosomally integrated, defective Type C retroviral vector was rescued from human D54 glioma (D54/GFP.neo) or rat 9L gliomblastoma (9L/GFP.neo) cells by transcomplementing with adeno-retrovirus chimeras. The model retroviral vector was constructed as described above and contained the green fluorescence protein gene (GFP) driven by the 5' LTR, followed by the internal ribosome entry site (IRES) of EMCV and the G418$^r$ gene as markers. Gag.pol and env functions were provided by adenoviruses expressing Moloney murine leukemia virus gag-pol (Ax.gag.pol) and the Vesicular stomatis virus envelope G-protein (Ax.VSV-G) under the tight control of an additional adenovirus expressing a reverse tetracycline transactivator (AVC2.rtTA). Together these chimeric viruses can be used to efficiently rescue/amplify the GFP.neo provirus, as measured by transduction of TE671 target cells and FACS analysis for GFP and resistance to G418.

This model system was used to optimize transduction conditions and tetracycline induction for retrovirus rescue. Infection of cells with the adenovirus expressing gag.pol, and subsequent exposure to tetracyclines showed greater than 40 fold induction of reverse transcriptase (RT) activity. Similarly, rescue of virus was strictly dependent upon addition of tetracyclines (greater than 100-fold induction by FACS). Infection of D-54/GFP.neo cells with optimized amounts of each adenovirus and exposure to transactivator resulted in 60% rescue of the integrated retrovirus using 100 nm doxycycline, and 80% using 1 $\mu$M doxycycline. Selection with G-418 resulted in retroviral titers of approximately $10^6$ cfu/ml. Supernatants of cells transduced with individual transcomplementing adenoviruses or in the absence of transactivator showed no detectable retrovirus.

What is claimed is:

1. A system for producing a secondary virus in producer host cells for subsequent infection of target cells, said system comprising a chimeric primary virus or a combination of viruses which either individually or collectively are genetically competent to direct the production in the producer host cells of the secondary virus, wherein the secondary virus is any virus other than the primary virus and is selected from the group consisting of a togavirus and a retrovirus.

2. The system of claim 1, wherein the producer host cells are autologous producer host cells and the target cells are autologous target cells.

3. The system of claim 1, wherein the secondary virus is isolated from the producer host cells.

4. The system of claim 1, wherein the secondary virus is replication deficient.

5. The system of claim 1, wherein the secondary virus comprises an expression cassette comprising a nucleic acid encoding a heterologous protein or an antisense nucleic acid.

6. The system of claim 5, wherein the secondary virus comprises an expression cassette comprising a nucleic acid encoding a protein selected from the group consisting of hormones, cell receptors, and enzymes.

7. The system of claim 5, wherein the secondary virus comprises an expression cassette comprising a nucleic acid encoding a protein selected from the group consisting of Factor IX and CFTR.

8. The system of claim 1, wherein the secondary virus comprises a nucleic acid that integrates into the genome of the target cells.

9. The system of claim 1, wherein the primary virus is an adenovirus.

10. The system of claim 1, wherein the secondary virus is a togavirus.

11. The system of claim 10, wherein the secondary virus is an alphavirus.

12. The system of claim 11, wherein the secondary virus is selected from the group consisting of Semliki forest virus (SFV) and Sindbis virus.

13. The system of claim 1, wherein the secondary virus is a retrovirus.

14. The system of claim 13, wherein the secondary virus is selected from the group consisting of oncornaviruses and lentiviruses.

15. The system of claim 1, wherein the target cells are selected from the group of consisting of embryonic cells and sperm cells.

16. A method for producing a secondary virus in producer host cells for subsequent infection of target cells, said method comprising:
   (i) contacting the producer host cells with chimeric primary viruses which individually or collectively are able to direct the production of the secondary virus in the producer host cells; and
   (ii) incubating the producer host cells for a time sufficient for the chimeric primary viruses to infect the producer host cells and to direct the production of the secondary virus for infection of target cells;
      wherein the secondary virus is any virus other than the primary virus and is selected from the group consisting of a togavirus and a retrovirus.

17. The method of claim 16, wherein the producer host cells are autologous producer host cells and the target cells are autologous target cells.

18. The method of claim 16, further comprising the step of infecting target cells with the secondary virus, followed either by integration of the viral genome or by production of a lytic infection.

19. The method of claim 16, further comprising the step of isolating the secondary virus.

20. The method of claim 16, wherein the secondary virus is replication deficient.

21. The method of claim 16, wherein the secondary virus comprises an expression cassette comprising a nucleic acid encoding a heterologous protein or an antisense nucleic acid.

22. The method of claim 21, wherein the secondary virus comprises an expression cassette comprising a nucleic acid encoding a protein selected from the group consisting of hormones, cell receptors, and enzymes.

23. The method of claim 21, wherein the secondary virus comprises an expression cassette comprising a nucleic acid encoding a protein selected from the group consisting of Factor IX and CFTR.

24. The method of claim 16, wherein the secondary virus comprises a nucleic acid that integrates into the genome of the cells.

25. The method of claim 16, wherein the primary viruses are adenoviruses.

26. The method of claim 16, wherein the secondary virus is a togavirus.

27. The method of claim 26, wherein the secondary virus is an alphavirus.

28. The method of claim 27, wherein the secondary virus is selected from the group consisting of Semliki forest virus (SFV) and Sindbis virus.

29. The method of claim 16, wherein the secondary virus is a retrovirus.

30. The method of claim 29, wherein the secondary virus is selected from the group consisting of oncornaviruses and lentiviruses.

31. The method of claim 16, wherein the target cells are selected from the group consisting of embryonic cells and sperm cells.

32. A method of rescuing an unknown viral genome from a host cell, said method comprising the steps of:
   (i) contacting the host cell with chimeric primary viruses which individually or collectively are able to package the unknown viral genome in the host cell to produce a replication deficient secondary virus;

(ii) incubating the host cell for a time sufficient for the chimeric primary virus to infect the host cell and to produce packaging components; and (iii) rescuing the unknown viral genome by the unknown viral genome to produce the replication deficient secondary virus, wherein the secondary virus is any virus other than the primary virus and is selected from the group consisting of a togavirus and a retrovirus.

33. The method of claim 32, further comprising the step of isolating the unknown viral genome.

34. The method of claim 32, further comprising the step of infecting a target cell with the replication deficient secondary virus.

35. The method of claim 32, wherein the primary viruses are adenoviruses.

36. The method of claim 32, wherein the unknown viral genome is a retrovirus.

37. The method of claim 36, wherein the unknown viral genome is selected from the group consisting of oncornaviruses and lentiviruses.

38. A system for producing a secondary virus in complementary producer host cells for subsequent infection of target cells, said system comprising chimeric primary viruses or a combination of viruses which in combination with the complementary producer cells are genetically competent to direct the production in the complementary producer host cells of a secondary virus, wherein the secondary virus is any virus other than the primary virus and is selected from the group consisting of a togavirus and a retrovirus.

39. A method for producing a secondary virus in complementary producer host cells for subsequent infection of target cells, said method comprising:

(i) contacting the complementary producer host cells with chimeric primary viruses which in combination with the complementary producer host cells are individually or collectively able to direct the production of the secondary virus in the complementary producer host cells; and (ii) incubating the complementary producer host cells for a time sufficient for the chimeric primary viruses to infect the complementary producer host cells and to direct the production of the secondary virus for infection of target cells;

wherein the secondary virus is any virus other than the primary virus and is selected from the group consisting of a togavirus and a retrovirus.

* * * * *